United States Patent [19]

Harms et al.

[11] Patent Number: 5,580,840
[45] Date of Patent: Dec. 3, 1996

[54] METHOD AND COMPOSITION FOR PRESERVATION OF CUT FLOWERS

[75] Inventors: David J. Harms, Naperville; Abdul R. Y. Meah, Justice, both of Ill.

[73] Assignee: Donlar Corporation, Bedford Park, Ill.

[21] Appl. No.: 439,279

[22] Filed: May 11, 1995

Related U.S. Application Data

[63] Continuation-in-part of Ser. No. 313,436, Sep. 27, 1994, which is a continuation-in-part of Ser. No. 972,375, Nov. 5, 1992, Pat. No. 5,350,735.

[51] Int. Cl.$^6$ ................................................ A01N 3/02
[52] U.S. Cl. ................................................ 504/115
[58] Field of Search ................................................ 504/115

[56] References Cited

U.S. PATENT DOCUMENTS

| | | | |
|---|---|---|---|
| 4,172,072 | 10/1979 | Ashmead | 260/115 |
| 4,799,953 | 1/1989 | Danzig et al. | 71/98 |
| 4,813,997 | 3/1989 | Kinnersley et al. | 71/66 |
| 4,839,461 | 6/1989 | Bochmke | 528/363 |
| 4,863,506 | 9/1989 | Young | 71/113 |
| 4,863,898 | 9/1989 | Ashmead et al. | 514/6 |
| 5,059,241 | 10/1991 | Young | 71/106 |
| 5,350,735 | 9/1994 | Kinnersley et al. | 504/147 |

OTHER PUBLICATIONS

Agri Finance, Apr. 1993, *Technological breakthrough on fertilizer use*, pp. 16–17.
Kinnersley et al., Plant Growth Regulation 9:137–146 (1990).
Byrnes, Fertilizer Research 26:209–215 (1990).
Farm Chemicals Handbook, 1987, Meister Pub. Co., Willoughby, Ohio, p. B10.

*Primary Examiner*—S. Mark Clardy
*Assistant Examiner*—Brian G. Bembenick
*Attorney, Agent, or Firm*—Zarley, McKee, Thomte, Voorhees, & Sease

[57] ABSTRACT

A method of preserving cut flowers such as roses, tulips, carnations and mums, by the insertion of the freshly cut stems of cut flowers in a solution of a water-soluble polyamino organic acid, preferably polyaspartic acid. The life of a flower, as it appears healthy and viable without stem bending or senescence of the flower itself, is substantially prolonged, in many cases two to three times longer than untreated flowers.

6 Claims, 4 Drawing Sheets

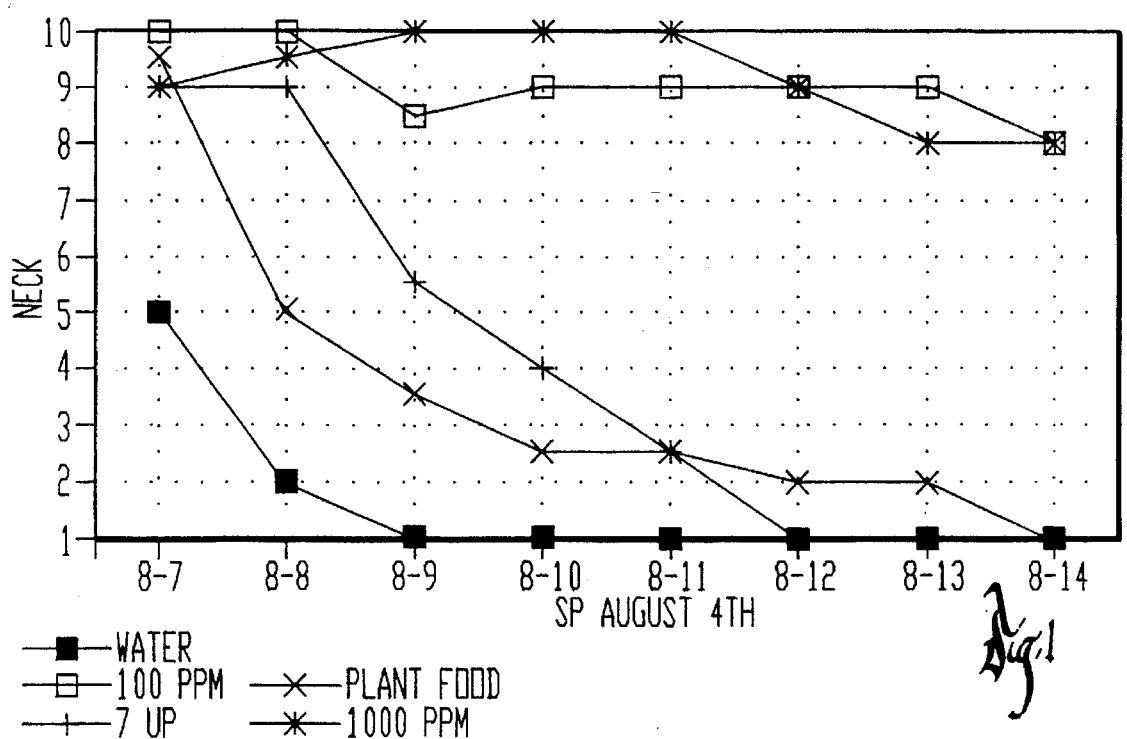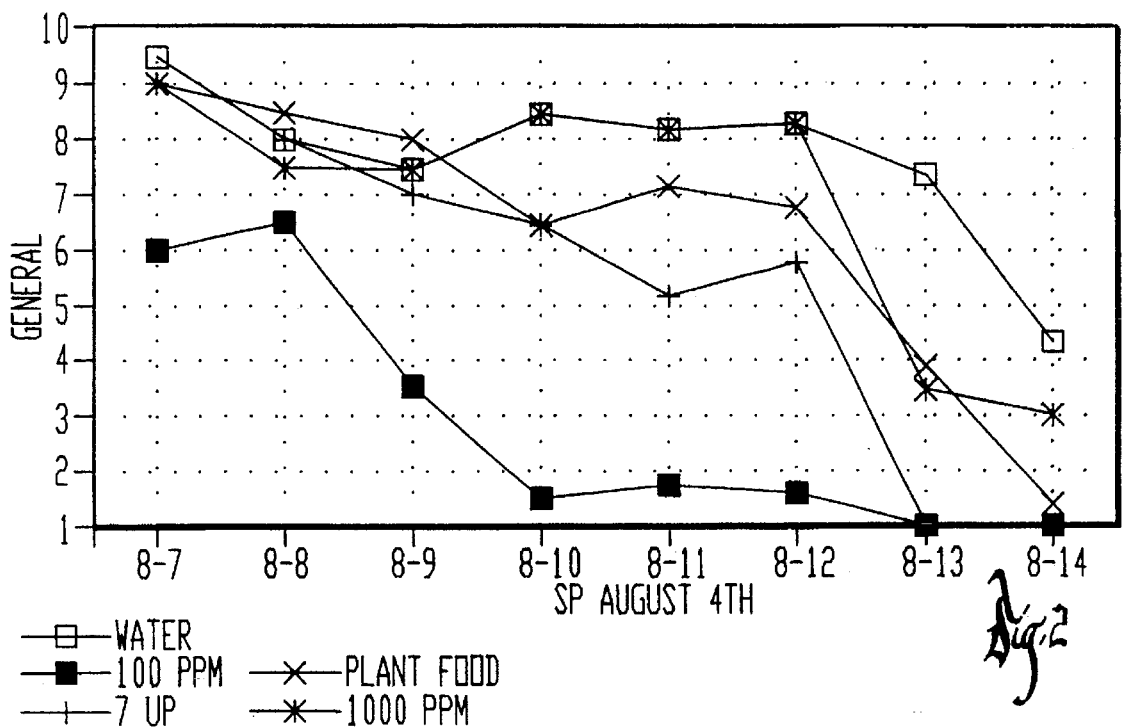

METHOD AND COMPOSITION FOR PRESERVATION OF CUT FLOWERS

CROSS REFERENCE TO A RELATED APPLICATION

This application is a continuation-in-part of patent number 08/313,436 filed Sep. 27, 1994, entitled "Method For More Efficient Uptake Of Plant Growth Nutrients", which itself is a continuation-in-part of Ser. No. 972,375 filed Nov.5, 1992, entitled "Composition And Method For Enhanced Fertilizer Uptake By Plants", now U.S. Pat. No. 5,350,735 issued Sep. 27, 1994.

BACKGROUND OF THE INVENTION

This invention relates to treating compositions for preserving fresh cut flowers in order to prolong the period that the flowers look natural and viable. In other words, to delay senescence of the flower and bending of the stem.

The business of fresh cut flowers is a multi-million dollar business. Necessarily, the longer that fresh cut flowers last in a vase or flower arrangement, the longer the purchaser has to enjoy those flowers. It is therefore an advantage to commercial producers as well as to the flower purchasers to treat fresh cut flowers in such a manner that they last as long as possible. A pleased consumer purchaser is likely to make a repeat purchase from the same flower shop.

Accordingly, it can be seen that there is a real and continuing need for effective preservation formulations to preserve fresh cut flowers which significantly delays the onset of stem bending and flower senescence. This invention has as its primary objective the fulfillment of this need.

In addition, another objective of the present invention is to provide a medium which preserves fresh cut flowers so that they can be enjoyed by the user for substantially longer periods of time than in the past.

Another further objective of the present invention is to provide a method and composition for general applicability to roses, tulips, carnations, mums and other flowers to preserve the flowers in their naturally-appearing viable state for longer periods of time.

An even further objective is to provide an economical non-toxic, biodegradable and environmentally friendly treating composition which does not rely upon expensive additives.

The method and manner of accomplishing each of the above objectives as well as others will become apparent from the detailed description of the invention.

SUMMARY OF THE INVENTION

A method of preserving fresh cut flowers so that droop and senescence are delayed which involves insertion of the freshly-cut stems of the cut flowers into a nutrient media that contains polyamino organic acid, preferably at a level of from about 100 parts per million to about 1000 parts per million. The preferred polyamino acid is polyaspartic acid. The treatment is effective on flowers generally, and is especially adapted for roses, tulips, carnations and mums.

BRIEF DESCRIPTION OF THE DRAWINGS

FIG. 1 is a graph illustrating the effect of polyaspartic acid in combination with plant food on roses as measured by drooping or stem bending.

FIG. 2 is a similar graph for polyaspartic acid and plant food on roses measuring the onset of senescence of the flower.

DETAILED DESCRIPTION OF THE INVENTION

Figure 3:
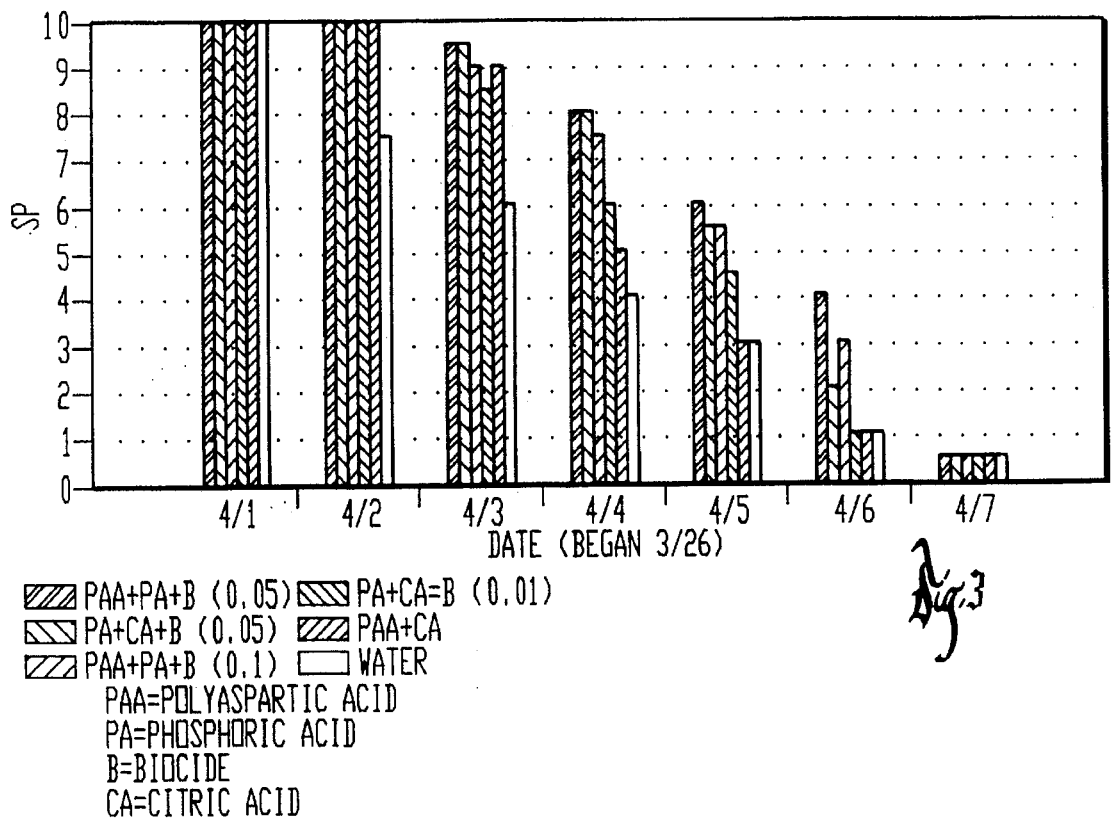
FIG. 3 shows data for onset of senescence for tulips, both treated and controls.
Figure 4:
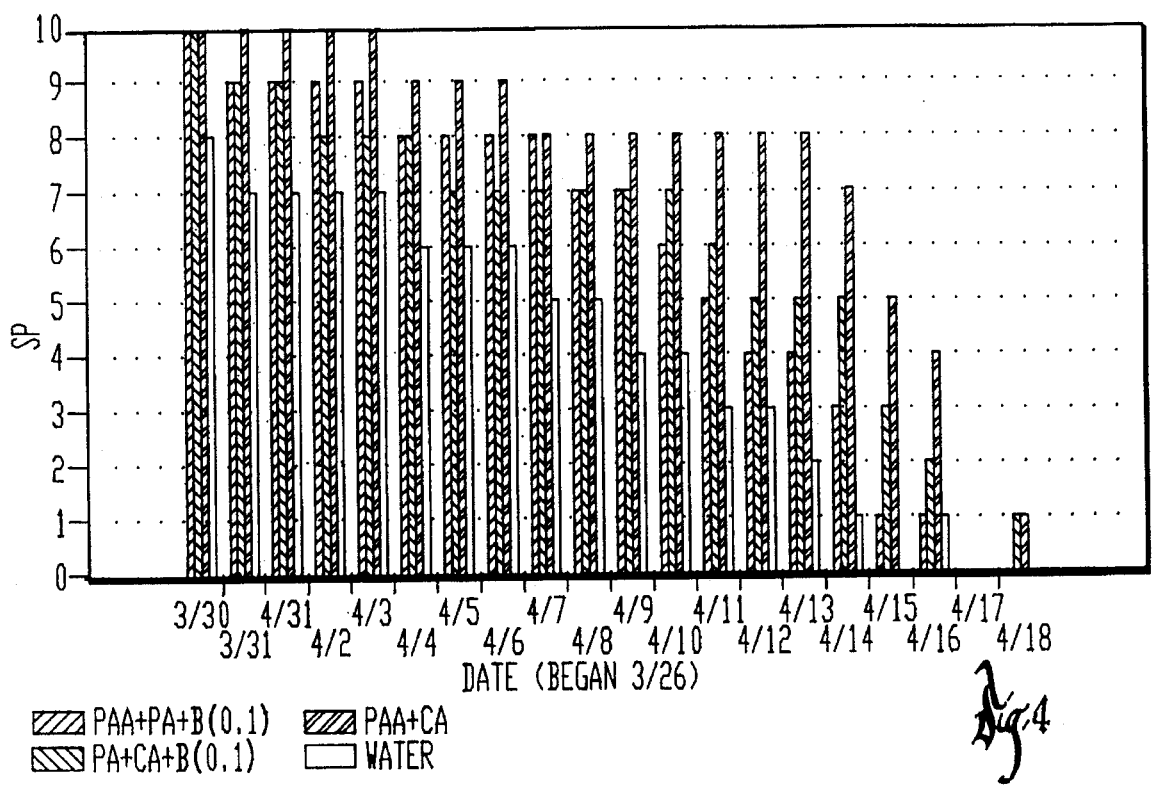
FIG. 4 shows data for onset of senescence for mums, both treated and controls.

In accordance with the present invention, viability of fresh cut flowers is extended using a nutrient solution for the fresh cut flowers which contains a water-soluble, polymeric amino acid. It surprisingly prolongs the fresh cut appearance of cut flowers, in many cases up to two to three times as long as normal, over flowers that do not have the treatment.

In general, the polymeric organic amino acids can be made available to the plant in nutrient solutions containing at least about 0.1 parts per million (ppm) by weight, preferably about 0.1 to about 1,000 parts per million (ppm) by weight, more preferably about 1 to about 500 ppm by weight, of the polymeric organic acid in the solution. Such solutions can be applied to the nutrient solution for uptake via the plant stem. Solutions containing the polymeric organic acid can be applied to contact the fresh cut stems, or leaves of the plants in amounts as discussed below. The preferred method, however, is stem uptake. Solutions containing the polymeric organic amino acid are also useful in conjunction with certain other plant nutrients as illustrated in the examples.

The polymeric organic acids, to be suitable for the practice of the present invention, must be water soluble, non-aromatic, and must have a molecular size sufficiently large to preclude absorption into the plant's own system. To that end, the non-aromatic polymeric organic acid units (residues), or mers, in the linear polymer chain constitutes the polymeric acid. Such linear polymer chains can be cross-linked, if desired, but only to a degree that does not materially affect the water solubility of the polymeric moiety. Polymeric organic acids having a molecular weight in excess of about 100,000 usually do not exhibit adequate solubility in water for the present purposes, thus for present purposes a polymeric organic acid molecular size not larger than about 100,000 is preferred. Particularly preferred molecular weight is in the range of about 2,000 to about 30,000.

Illustrative are polymeric organic acids, with or without carboxylic acid, thiocarboxylic acid, imidocarboxy, and/or amino side chains, such as, for example, polyacrylic acid, polymaleic acid, polylysine, polyglutamic acid, polyaspartic acid, polyglycine, polycysteine, polycysteine/glutamic acid, mixtures of the foregoing, and the like. Block or random copolymers or terpolymers of several organic acids are also within the purview of the present invention as the polymeric acid component thereof. For example, the utilized polymeric acid component can be a block copolymer of aspartic acid residues and L-lactic acid residues, a random copolymer of aspartic acid residues and glycolic acid residues, a conjugated protein constituted by amino acid residue chains interconnected by one or more polycarboxylic acid residues, a copolymer of acrylic acid, acrylamide, maleic acid and the like.

Polymers of organic acids are commercially available. In addition, such polymeric acids, especially polyamino acids, can be made, inter alia, by thermal condensation methods. See, for example, U.S. Pat. No. 5,057,597 to Koskan, Little et al., American Chemical Society 97:263–279 (1991), and U.S. Pat. No. 4,696,981 to Harada et al.

The starting materials for the polymerization, i.e., the organic acids, can exist as optical isomers, depending upon their respective structures, and can be polymerized either as a racemic mixture or as segregated optical isomers.

A racemic mixture is an equal molar mixture of the two possible optical isomers—the levorotatory and dextrorotatory isomers. Levorotatory (l) isomers are isomers of an optically active compound which rotate a beam of polarized light to the left; the dextrorotatory (d) isomers are isomers of the same compound which rotate a beam of polarized light to the right. Another convention employed to define the configurational relationships of dissimilar functional groups bonded to an asymmetric carbon atom, the so-called Fischer Method, is based on the geometric arrangement of functional groups relative to each other rather than on the direction (left or right) in which a standard solution of the compound rotates a beam of polarized light. The Fischer Method is well known in the art, and is discussed in more detail in Ficser & Ficser, *Introduction to Organic Chemistry*, D.C. Heath and Co., Boston, Mass., (1957) at pages 209–215. The Fischer Method designations are used herein.

In accordance with the Fischer Method, any compound which contains an asymmetric carbon atom of the same configuration as the asymmetric carbon in the arbitrary standard, dextrorotatory glyceraldehyde, is classified in the D series, while compounds in which the asymmetric carbon atom has the opposite configuration are classified in the L series. Although the Fischer D and L classifications do not correlate with dextro-(d) and levorotatory (l) optical activity for all compounds, those classifications can be used in combination with the optical activity classifications d and l to define both the geometric arrangement and specific optical activity of any optically active isomer. Thus, the L-isomer of lactic acid, which is dextrorotatory, is defined as L-9d)-lactic acid, and the D isomer is defined as D(l)-lactic acid. However, both of these characteristics of relatively simple compounds can be adequately defined by reference to only one classification system. For example, L-lactic acid is known to be dextrorotatory and l-lactic acid is known to have the D configuration according to Fischer. For this reason, the D and L isomers of lactic acid and other relatively simple organic acids are usually identified only by the D and L designations, and without explicit reference to their optical activity.

For organic acids that exhibit optical activity, the polymers and copolymers of the L-isomers are preferred. However, racemic mixtures as well as polymers and copolymers of the D-isomers can be utilized for the present purposes.

In some instances either the L-form or the D-form may exhibit greater biological activity vis-a-vis plant growth promotion. In such instances the more active form is, of course, the preferred form.

Particularly well suited for the practice of the present invention are the non-chelating polyorganic acids such as polyacrylic acid and the like, as well as the polyamino acids such as polyaspartic acid having a molecular weight in the range of about 3,000 to about 28,000, polyglutamic acid having a molecular size in the range of about 4,000 to about 14,000, polyglycine having a molecular weight in the range of more than 1,500 to about 7,000, and polylysine having a molecular size in the range of about 2,000 to about 7,000.

The amount of polyaspartic acid in the treating composition can vary widely, but satisfactory results are obtained when it is from about 100 parts per million to about 1,000 parts per million, preferably from about 1 part per million to about 500 parts per million. It may be used alone or in combination with known nutrients or additives such as citric, phosphoric or acetic acid or suitable salts thereof and biocides. If desired, agents may also be added to enhance wetting or capillary action up the plant stem.

Also, in the preservation of freshly cut plants, aqueous gels formed from the mixed salt polymers of aspartic acid are of sufficient strength to support the stem of the plant even in the absence of inert solid aggregates. In addition, the polymers used in the method of the present invention possess sufficient water-absorbing and swelling ability such that suitable gels are formed using very low percentages of polymers, therefore allowing a sufficient amount of free, unbound water available for plant uptake upon demand.

In addition to clays and natural gums, several types of water-absorbing cross-linked polymers have been used to form aqueous gels that are useful as a plant growth medium or plant preservation medium. However, the previous methods and compositions all possess disadvantages that severely limit their practical utility. For instance, gels made from clays are often difficult and messy to prepare; polymers based on natural gums or natural polymers, such as starch, are subject to chemical and bacterial degradations; some polymers must be used in a high percentage and may bind the water to such a degree that sufficient water is not available for use by the plant; polymers incapable of surrendering the water from the gel to the plant must be combined with inert solid aggregates in order to free some water for use by the plant; and some of the polymers utilized to make the gels are expensive and difficult to prepare.

The flowers that may be used with the present invention include virtually any flower that is commonly sold as fresh cut. Particularly satisfactory results are achieved with roses, tulips, carnations, and mums, but other flowers such as gladiolus, baby's breath, daisies, orchids, lilies, iris, snapdragons, but not limited to, may be employed.

While any of the great number of additional nutrients known to the art may be used in the present treatment composition, the nutrients generally employed consist mainly of sugar, such as sucrose or dextrose. This is employed as a base material to which the other ingredients are added in the desired quantities and proportions.

The sugar provides a source of nutrition capable of being utilized by the flower or other plant so that it will continue to mature and develop. Either sucrose or dextrose or combinations thereof (as well as other sugars) may be employed. However, the preferred nutrient is sucrose, particularly where the composition is to be used in the treatment of roses.

The desired effects of the polyamino acid are also enhanced as earlier indicated by the use of a small amount of wetting agent of the non-ionic type. The wetting agents known under the name "Tween", sold by the Atlas Powder Company and said to be polyoxyethylene derivatives of hexitol anhydride partial long chain fatty acid esters, have been found to be especially suitable. The wetting agent must be compatible with the other ingredients of the composition and must not adversely affect plant life. The quantity of wetting agent must be limited, since too much wetting agent has been found to prevent absorption by the flower stem, resulting in rapid wilting. With wetting agents of the "Tween" type, the upper limit is about 25 ppm with lesser amounts providing better results.

The wetting agent also insures that the water-conducting vessels and tissues of the flower stem will remain open in order for the blossoms to draw nutrient when necessary.

The following examples are offered to further illustrate, but not limit the process of this invention.

EXAMPLES

Several tests were conducted at different dates and with various types of cut flowers, some using added nutrients, and some using no treatment. Favorable response was obtained with various mixtures of polyaspartic acid and various additional additives. Individual flowers were placed in vials containing polyaspartic acid and nutrient solutions. Each was rated for general appearance or senescence and for bending of the stem each consecutive day. The experiment in FIGS. 1 and 2 was begun on Aug. 4th with the first reading taken on Aug. 7th. In this experiment (using roses), the effect of stem bend was delayed by approximately seven days, and good general appearance was maintained for four additional days with the addition of either 100 ppm or 1,000 ppm of polyaspartic acid. Comparison lines for water, 7 Up and a commercially-used product were used for controls.

Figure 5:
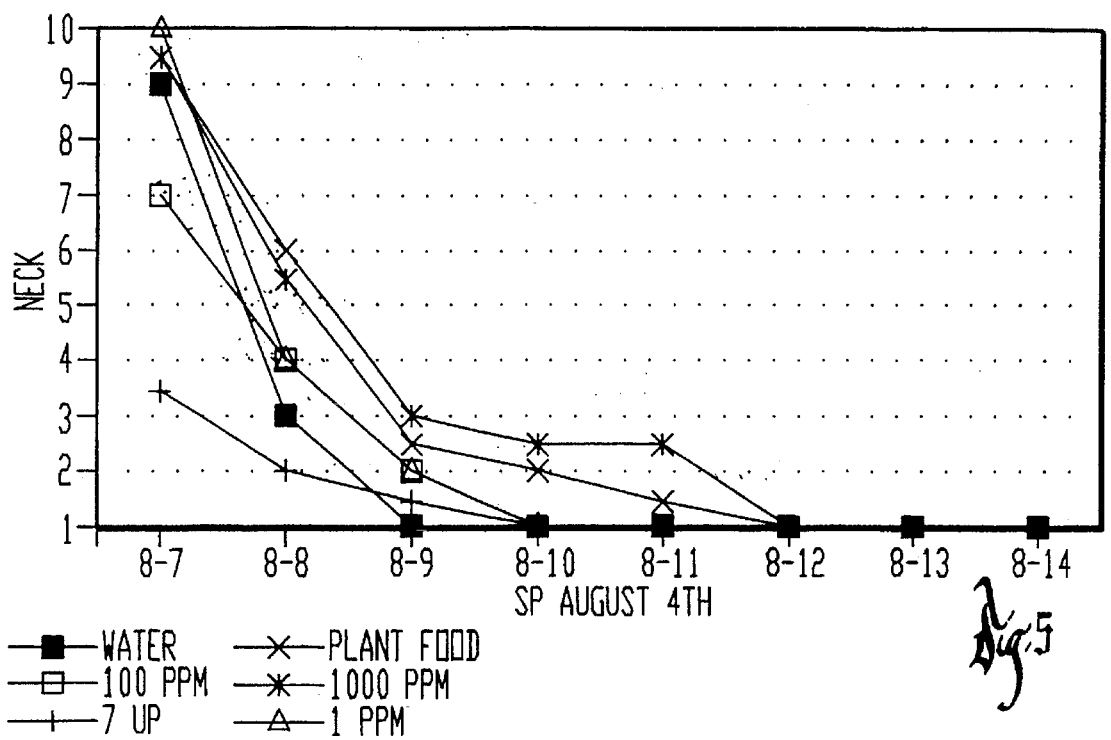
FIG. 5 shows polyaspartic acid at various dosages for treatment of roses and the effect on stem bending.
Figure 6:
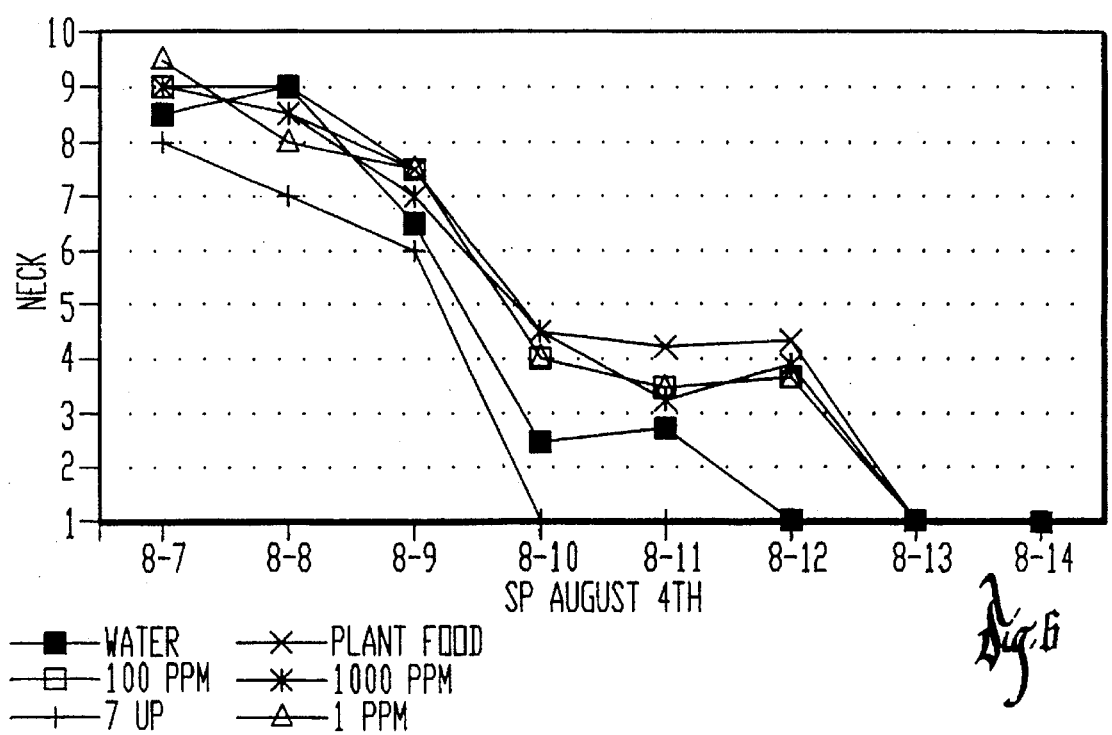
FIG. 6 shows polyaspartic acid at various dosages for treatment of roses and the effect on general senescence.
Figure 7:
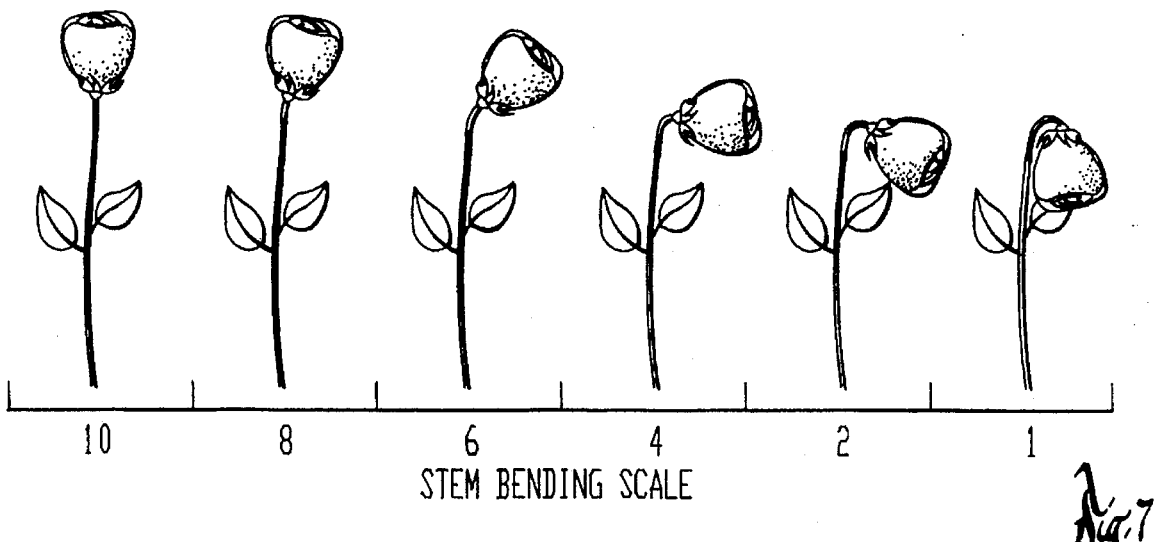
FIG. 7 shows the grading scale for stem bending.

In particular in FIGS. 1 and 2, on Aug. 4, the inventors initiated a study to evaluate polyaspartic acid in combination with tap water, 7 Up, and a commercial plant food (Floralife). Roses were placed in solutions and rated daily for general appearance and degree of stem bending over an eight-day period. Note in FIGS. 1 and 2, after three days the roses in tap water were no longer acceptable, and after four days those in plant food alone had necks bent at a right angle. When polyaspartic acid was added to a mixture of plant food, the roses stayed upright for ten days and the general appearance was acceptable for eight days. Note in FIGS. 5 and 6 polyaspartic acid in tap water alone did not show near the positive results as it did in combination with plant food for either bent neck (FIG. 5) or general appearance (FIG. 6).

Later, the 5,000 and 2,000 molecular weight formulations were tested with plant food. Both gave excellent results when used with citric acid and plant food. Rates from 10 ppm to 1,000 ppm continued to give positive responses throughout the test.

Still later we ran similar tests with various combinations of citric acid, phosphoric acid, biocide and levels of polyaspartic acid. There seemed to be no difference between citric acid and phosphoric acid when combined with polyaspartic acid and biocide. There was no obvious difference between the 10, 100 and 1000 ppm levels of polyaspartic acid.

These experiments were performed on various cut flowers including: roses, tulips, mums, and carnations. Results varied between different classes of flowers; however, all classes showed benefit with some combination of polyaspartic acid, with conventional nutrients.

In those experiments using plant food, the plant food was Floralife, a commercially available nutrient with a pH adjusted to 4.5 with citric acid or phosphoric acid.

In each of the above examples it can be seen that the data illustrates that the invention accomplishes its stated objectives.

What is claimed is:

1. A method of preserving fresh cut flowers so that droop and senescence are delayed, said method comprising: insertion of the freshly cut stems of cut flowers into a treatment solution containing a small but flower preserving effective amount of a water-soluble, non-aromatic polyorganic acid which is a polyamino acid of the group consisting of polyaspartic acid, polyglutamic acid, polyglycine, polylysine, a copolymer of cysteine and glutamic acid, and a terpolymer of cysteine, glutamic acid and aspartic acid, said polyamino acid having at least a molecular weight larger than 1,500, wherein the treatment solution contains additional nutrients and additives.

2. The method of claim 1 wherein the polyamino acid is polyaspartic acid.

3. The method of claim 1 wherein the amount of polyamino acid is from about 0.1 ppm to about 1,000 ppm.

4. The method of claim 1 wherein the amount of polyamino acid is from about 1 ppm to about 500 ppm.

5. The method of claim 1 wherein the flowers are selected from the group consisting of roses, tulips, carnations, mums, baby's breath, daisies, gladiolus, orchids, lilies, iris, and snap dragons.

6. The method of claim 1 wherein added nutrients and additives include citric acid, phosphoric acid and various forms of sugars and biocides.

\* \* \* \* \*